United States Patent [19]

Jeffer et al.

[11] Patent Number: 5,513,988
[45] Date of Patent: May 7, 1996

[54] METHOD OF LINING A VOID IN A DENTURE OR APPLYING A LINER AROUND AN IMPLANT CYLINDER OR IMPLANT HEALING CAP

[75] Inventors: Peter H. Jeffer, New York, N.Y.; Richard F. Dettro, Newark, Del.; Harold DeHaven, Jr., West Chester, Pa.

[73] Assignee: Nu-Dent, Inc., New York, N.Y.

[21] Appl. No.: 233,849

[22] Filed: Apr. 26, 1994

[51] Int. Cl.⁶ .............................. A61C 13/02; A61C 8/00
[52] U.S. Cl. ........................................ 433/168.1; 433/173
[58] Field of Search .................................. 433/167, 168.1, 433/169, 170, 171, 172, 173, 174, 175, 176, 177

[56] References Cited

U.S. PATENT DOCUMENTS

| | | | |
|---|---|---|---|
| 2,854,746 | 10/1958 | Lester et al. | 433/169 |
| 3,716,918 | 2/1973 | Tole . | |
| 3,808,686 | 5/1974 | Tauman et al. | 433/167 X |
| 3,969,303 | 7/1976 | Prosen | 433/168.1 X |
| 4,270,904 | 6/1981 | Bogaert | 433/167 |
| 4,514,173 | 4/1985 | Re | 433/178 |
| 4,764,115 | 8/1988 | Willits et al. | 433/172 X |
| 5,030,094 | 7/1991 | Nardi et al. | 433/169 |
| 5,037,473 | 8/1991 | Antonucci et al. | 433/168.1 X |
| 5,203,700 | 4/1993 | Chmel | 433/169 |
| 5,282,746 | 2/1994 | Sellers et al. | 433/172 |

*Primary Examiner*—Nicholas D. Lucchesi
*Attorney, Agent, or Firm*—Wallenstein & Wagner, Ltd.

[57] ABSTRACT

A known elastomeric methyl methacrylate-free soft material has been used as a denture reline material. The material includes powder and liquid components which are mixed together and cured. The invention involves new uses of the material. Where the invention involves lining over a void in an acrylic denture, the resultant mixture is applied over the underlying surface of the acrylic over the void to chemically and mechanically bond the mixture in a seamless bond to the underlying surface of acrylic. A liner is formed having the characteristics of being flexible, resilient, shape retentive, hydrophobic, soft, spongy and cushiony. A known sealer component is then applied over the liner to create a non-absorbent exterior surface seal and glaze. Where the method is used to apply a liner around an implant cylinder or an implant healing cap anchored into a jaw bone the resultant mixture is applied around the surface of the implant or healing cap for forming a liner or gasket around the implant or healing cap. The sealer component is then applied over the liner to create a non-absorbent surface seal and glaze.

21 Claims, 1 Drawing Sheet

METHOD OF LINING A VOID IN A DENTURE OR APPLYING A LINER AROUND AN IMPLANT CYLINDER OR IMPLANT HEALING CAP

BACKGROUND OF THE INVENTION

For decades, chemists and dental product manufacturers have attempted to develop a soft liner for dentures and/or prosthetic devices to absorb the pressure on the wearer's gums on the tissue side of these devices. The discomfort and often pain to the denture wearer necessitates shaping the hard acrylic or other surfaces so as to allow perfect fit.

Inasmuch as dimensional change in the size and shape of the jaw occurs in all denture wearers, (especially in older people or in post-operative cases when swelling subsides), a soft, flexible, custom fit, cushion like liner permanently bonded to the prosthesis is needed.

Whereas prior products exist intended to accomplish the above objectives, all have different problems associated with their application. In particular, the non-compatible soft liners such as the silicon or rubber-based materials must be "glued" onto the hard acrylic surface with an adhesive bonding agent, and often this bonding agent contains a methyl methacrylate monomer. Over time, these adhesive agents leach into the soft material and harden it.

Moreover, adhesives harden and crack at the "seam" at the junction where the soft material is glued on to the hard material. Lactic acid, alcohol, and/or medication accelerate this separation. At this point, bacteria, fungus, odor, debris, and stain penetrate the soft liners. This natural absorption degrades the soft liners creating a hardening, peeling, and medically unstable condition.

In addition, the repair process of other existing materials is difficult since the base material either flakes off when trimmed, or it cannot be re-molded with standard dental tools. Also, to "glue" small sections of liner onto thin acrylic edges is difficult or impossible as the liners break off under the constant pressure which occurs in the oral cavity.

There are various products which use heat or light to cure resins of various formulation onto prosthetic devices. Almost all of these formulations require a bonding agent which run into the same problems as mentioned above. Many of these finished liners absorb liquids accelerating their deterioration.

Another category of liners which are temporary in nature are known as "tissue conditioners". These gels or stick-on resins last only weeks or a few months before they peel-off. They usually are soft due to high porosity, and thus they absorb liquids which ultimately breakdown the materials. The absorbency allows bacteria and odor buildup in the mouth, an undesirable result.

An elastomeric material is available which overcomes many of the disadvantages of the prior indicated materials. This material is a methyl methacrylate-free soft material which effectively fuses to acrylic surfaces without a gluing agent. The material is formed by blending a powder component of polyethylmethacrylate and a liquid component of Di-n-butyl phthalate, ethyl acetate and ethyl alcohol which are mixed together until all of the powder particles are totally moistened. The resultant mixture is then applied as a reline material for dentures by being coated on the denture surface. A polyvinyl chloride/polyvinyl acetate copolymer dissolved in a methyl ethyl ketone solvent forms a sealer component which is then applied over the liner to create a nonabsorbent surface seal.

SUMMARY OF THE INVENTION

An object of this invention is to provide techniques for using the above noted methyl methacrylate-free material for purposes other than dental reline materials.

A further object of this invention is to provide methods for applying such a liner to voids in a denture or for utilizing such a material as a gasket around an implant cylinder and/or implant healing cap anchored into a jaw bone.

In accordance with this invention, the methyl methacrylate-free soft material is formed by blending the powder and liquid components in the known manner. In accordance with one practice of the invention, the material is used for lining over a void in a denture having an underlying surface of acrylic. This could be done, for example, where the void is a tooth anchor hole completely through the denture and a gasket is formed around the tooth anchor hole. Alternatively, the void could be a palatal tori which is covered by the material. The material could also be used to stabilize a partial denture by molding the saddle area to the residual ridge.

In an alternative practice of the invention the material could be used for applying a liner or gasket around an implant cylinder by applying the material around the surface of the implant to form a gasket. Alteratively, a gasket could be formed around an implant healing cap anchored into a jaw bone.

THE DRAWINGS

DETAILED DESCRIPTION

The present invention is based upon the recognition that the known elastomeric methyl methacrylate-free soft material described above could be used in techniques heretofore not practiced in the prior art. Thus while the prior art used such material as a reline material for dentures it was not previously recognized that the attributes of that material made it particularly useful for other dental techniques. It was also not previously recognized that the curing characteristics inherent with the material made it possible to apply the material at chairside to cure, for example, in only five minutes in the patient's mouth, although other conventional methods of curing may be used.

The characteristics of the elastomeric methyl methacrylate-free material make it particularly suitable for diverse various applications as a long lasting, soft, hydrophobic, cushion like material chemically bonded onto any acrylic surface using a hot water cure under water or air pressure.

The material fuses to the surface of acrylic by cross linking into the exterior pores thus establishing a chemical and mechanical bond. The material remains spongy soft, flexible, shape retentive, and permanently attached to the underlying hard material.

Figure 1:
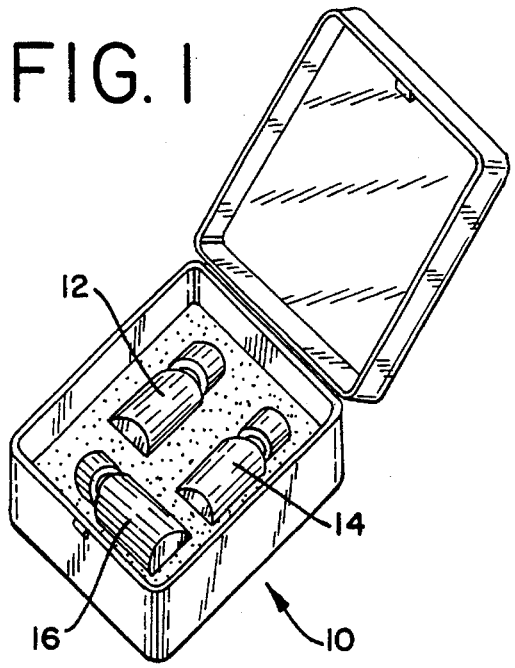
FIG. 1 is a perspective view of a kit for packaging the materials used in the methods of this invention.

The various components of the material can conveniently be prepackaged in a kit. FIG. 1, for example, illustrates such a kit 10 which could take any suitable form, such as being a carton in which the components would be packaged. Thus, as shown therein a bottle or container 12 could be used for a powder component while a liquid component could be packaged in a bottle 14. A sealer would be packaged in bottle or container 16. In the preferred practice two and one-half parts loosely packed powder from container 12 is mixed into one part of liquid from container or bottle 14 until all powder particles are thoroughly saturated.

Powder component in container 12 would be polyethylmethacrylate while the liquid component in bottle 14 would be Di-n-butyl phthalate, ethyl acetate and ethyl alcohol. The sealer in container 16 would be a polyvinyl chloride/polyvinyl acetate copolymer dissolved in a methyl ethyl ketone solvent component which would be capable of providing a non absorbent surface seal and glaze when applied over the mixture of the cured powder and liquid component. The hardness of the material could be controlled by controlling the amount of powder utilized in the mixture. Where more powder is used a more dense material results which in turn is harder. Material can be formed from its individual components for dental reline purposes by use of the following chairside technique:

1. Relieve undercuts, grind (1–2+)mm of space to receive material hollowing out entire tissue side of denture to allow room, especially where gum ridge peaks; Roughen peripheral roll & (3+)mm of the outer surface of denture; Clean & dry denture where reline applied;
2. Pour powder, (all at once), into liquid in a volume ratio of (2) to (2½) parts powder into (1) part liquid; Gently mix until all the powder particles are moistened; Consistency instantly turns "sticky" or "honey-like"; (Slightly more liquid thins the mix, increases working time, and makes a slightly softer reline);
3. Immediately, generously spatulate and spread the sticky mixture of material evenly onto totally dry denture surface;
4. Patient moistens lips with tongue as this material will not adhere to any saliva or wet covered areas; Insert the denture filled with material into patient's mouth; Have the patient close gently into occlusion for (1) minute as done for normal impression;
5. Remove denture from the mouth; Blend and taper excess material with finger coated with material liquid to completely overlap the peripheral roll (3+)mm onto acrylic surface. (Immediately cure);
6. Place denture in cup with relined side up, add steaming hot water (up to 165 degrees F.) for (15) minutes; For Pressure Pot cure; Fill pot to very top with hot water, place the cover on pot and water will overflow allowing no air bubbles; Turn screw knob till (25) PSI & cure for (15) min. OK if pressure slips as water cools;
7. Chill finished relined denture in cold water to temporarily harden soft liner; Remove excess flash with finishing stone or acrylic burr tapering reline on the labial and buccal surface; Finish with a wet rag wheel & pumice; High gloss not necessary;
8. It is important to apply a complete coat of sealer with brush or cotton tip applicator over the totally dry material soft liner; Material forms a non-absorbent, high gloss, stain resistance exterior surface; Sealer air dries in (2+) minutes—then, repeat with a second complete coating and allow to dry.

An advantageous property of the material is its curing characteristics. For example, as previously noted the material can be cured in 15 minutes in steaming hot water, at chairside or in a jig. Alternatively, the material could be cured in 45 minutes in a flask or in only 5 minutes in the mouth.

A particularly advantageous unique use of the material is for gasket anchoring. This could be done for retention of a denture as a gasket around the circumference of a pass-through hole for existing teeth. As illustrated the liner 24 is used for retention of a denture as a gasket 28 around the circumference of a pass through hole 30 for existing teeth. The hole 30 is enlarged to the desired size. Then the material is blended over, under and around the gasket hole 30, and onto surrounding acrylic surfaces 22. Then the liner is cured as described in Step 6 of the chairside technique.

Where the material is used as an implant gasket the following steps would be practiced:

1. Trim back and relieve the tissue side of temporary denture with any acrylic burr to allow for unobstructed seating initially over the tissue area, and again reline over the healing cap(s) when exposed;
2. Pour material powder, (all at once) into liquid in a volume ratio of (2) to (2½) parts powder into (1) part liquid; Gently mix until all the powder particles are moistened; Consistency instantly turns "sticky" or "honey-like"; (Slightly more liquid thins the mix, increases working time, and makes a slightly softer reline);
3. Immediately, spatulate sticky mixture of material into the dry tissue side of the denture previously reamed-out in Step (1); For large surface relines follow step 4a; For small surface relines & for relines over healing cap(s), when exposed, follow step 4b; 4a. Seat over tissue area; patient gently closes into centric occlusion for (1) minute; remove denture; taper & blend excess material with finger coated with material liquid to overlap the peripheral roll (3+)mm onto outer acrylic surface; Immediately, process in steaming hot water, (up to 165 degrees F) for (15) minutes; (for Pressure Pot cure, see Chairside Technique instruction, step #6) 4b. Seat over tissue area, and over healing cap(s), when exposed; Have patient close gently into centric occlusion for in-the-mouth cure in (5) minutes; Can also cure in steaming hot water in (15) minutes.
4. Post curing, chill finished reline in cold water to temporarily harden soft liner. Trim excess material using finishing stone & acrylic bur. Finish with a wet rag wheel & pumice for a smooth surface;
5. Apply two complete coats of Sealer over totally dry reline to form a non-absorbent, high-gloss surface, Sealer air dries in ((2+) min., and repeat with a second coat to repel fluids, bacteria, odor and stain.
6. For rebonding, adjustments, and refittings the previously noted chairside techniques would then be used.

Figure 6:
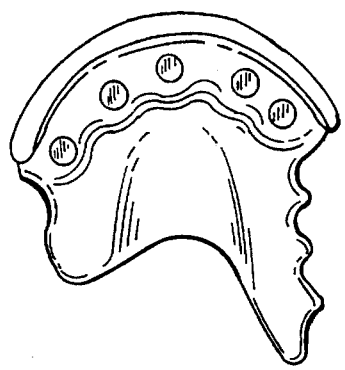
FIG. 6 is a bottom plan view of the material over the tissue and healing caps.

Because it has been recognized that the material could cure in the mouth in only five minutes the material advantageously lends itself to gasket anchoring. The material adheres to all acrylic surfaces and thus can be used to form a gasket around existing teeth for anchoring partial dentures or to anchor or cushion over dentures onto implant healing caps. FIG. 6 illustrates the reline material over the tissue and healing caps. Five such healing caps are shown. The coating of the cured material with the sealer provides a non-absorbent exterior surface so as to maintain the gasket's softness, and prevent discoloration, odor and bacteria ingress. No other polyethylmethacrylate resin uses this technique at the dentist's chairside by an in the mouth cure or in the dental laboratory using a hot water cure in 15 minutes. The present invention in one of its practices thus represents the only chairside method for gasket anchoring.

The use of less powder in the mix, (e.g. 2½:1) enables a slightly softer finished product. This application for use of this formulation includes a soft denture line, both partials and full dentures, and other prosthetic devices such as mouth guards and retainers.

Moreover, this formulation is ideal as a soft liner on the tissue side of a denture during the transitional healing period after installation of an implant.

Its hydrophobic nature minimizes bacterial ingress. Its adjustable softness allows a light functional load system for moderate vertical stress for osseointegration of the implant cylinder into the jaw bone.

Figure 2:
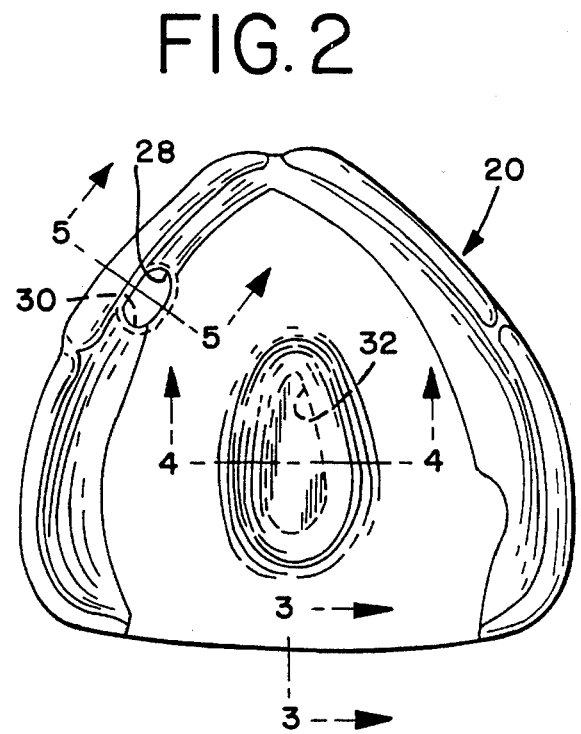
FIG. 2 is a plan view of a denture having the liner of the materials applied thereto.
Figure 3:
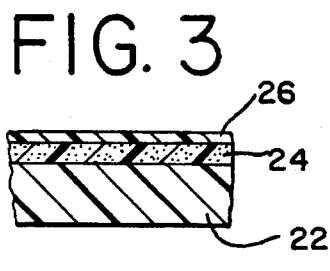
FIGS. 3–5 are cross-sectional views taken through FIG. 2 along the lines 3–3, 4–4 and 5–5, respectively.
Figure 4:
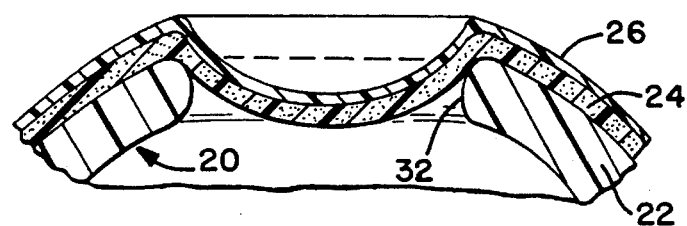
Figure 5:
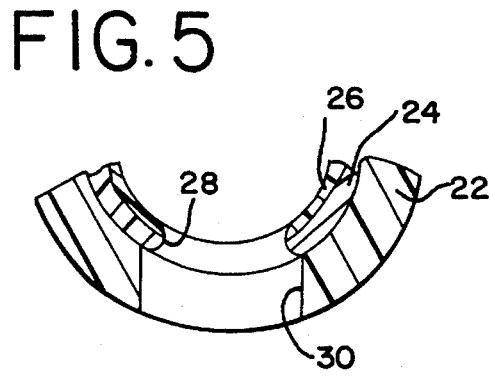

The unique chemical fusion allows extension over large voids 32 on denture surfaces for use in palatal tori such as shown in FIGS. 2 and 4. The material can be used as a gasket retentive liner 28 bonded around the circumference of a hole 30 (such as shown in FIGS. 2 and 5) and onto the surrounding acrylic surfaces to anchor the denture to a patient's existing teeth. It can be used over the peripheral roll of denture and bonded onto the outer acrylic surface of a denture to permit seamless surfaces and soft, flexible exterior edges. The material bonds onto itself to permit obturator of almost any height for patients with cleft palates.

These blended liquids of sealer 26 air dry in two minutes establishing a hydrophobic, non-absorbent, high-gloss, stain resistant, surface finish. This step is repeated for a stronger external bond. No other soft line product uses such a sealer.

The finished soft relined surface will remain soft for multiple years, even in the oral cavity. The use of the sealer 26 effectively prevents lactic acids, bacteria, fungus and other substances from penetrating the hydrophobic soft reline. Thus, internal degradation does not occur as the sealer 26 keeps out acidic fluids.

The lack of a seam at the junction where the soft reline is bonded onto the hard acrylic prevents separation of the soft material from the hard acrylic. The material is blended over the peripheral roll of the denture onto the surrounding acrylic surface, for more surface contact and thus a better and more permanent chemical bond.

Since no methyl methacrylate or bonding agent is used in this procedure, the leeching of methyl methacrylate into the soft material does not occur keeping the liner softer for a longer period of time. The specific method of mixing, application, and curing in hot water under 25 PSI of pressure accelerates the bonding of the soft material onto the acrylic. The tolerance of temperature extends up to 165° F. and the pressure can vary from 15 PSI to 40 PSI for the same results.

The material is not glued onto the acrylic, thus the versatility of applications expands dramatically, i.e. for gasket retentive liners, for palatal tori, for obturator cases, and for partial dentures, etc.

The material can be used to stabilize a partial by molding the saddle area to the residual ridge. Its unique, flexible "memory" enables it to grip undercuts, to help anchor partial dentures.

The material can be trimmed using standard dental tools; and, it rebonds to itself for fast, simple repairs. Re-sealing of the exterior surface should be initiated once per year. To reseal, (1) the existing surface sealer is ground off, (2) the surface is smoothed, (3) the surface is dried, and (4) a new coat of sealer is painted on.

Although the invention has been described with respect to a specific known elastomeric methyl methacrylate-free material, the invention may be broadly practiced with other materials, particularly elastomerics, having like characteristics.

The invention thus provides dental techniques based upon unobvious uses of the known material by recognizing that various characteristics of that material lend itself to such uses.

What is claimed is:

1. A method of lining over a void in a denture having an underlying surface of acrylic including the steps of (i) blending the components of an elastomeric material to form a resultant mixture, and (ii) applying the resultant mixture over the underlying surface of acrylic over the void to chemically and mechanically bond the mixture in a seamless bond to the underlying surface of acrylic to form a liner having the characteristics of being flexible, resilient, shape retentive, hydrophobic, soft, spongy and cushiony.

2. The method of claim 1 wherein the elastomeric material is a methyl methacrylate free material.

3. The method of claim 1 including applying a sealer over the liner to create a non-absorbent exterior surface seal and glaze.

4. The method of claim 1 wherein the components comprise a powder component and a liquid component which are mixed until all of the powder particles are totally moistened.

5. The method of claim 4 wherein the powder component is polyethylmethacrylate, the liquid component being Di-n-butyl phthalate, ethyl acetate and ethyl alcohol, and the sealer being a polyvinyl chloride/polyvinyl acetate copolymer dissolved in a methyl ethyl ketone solvent.

6. The method of claim 1 wherein the void is a tooth anchor hole completely through the denture, including forming a gasket around the tooth anchor hole in the denture from the liner and sealer component.

7. The method of claim 6 wherein the mixture is blended over and under and around the anchor hole and onto the adjacent underlying surface of the denture.

8. The method of claim 1 wherein the void is a palatal void, including covering the palatal void in the denture with the liner and sealer component.

9. The method of claim 1 wherein the void is the saddle area of a partial denture and the partial denture is stabilized by molding the saddle area to the residual ridge.

10. The method of claim 1 wherein the method is carried out at dental chairside.

11. The method of claim 10 wherein the resultant mixture cures in the mouth in about 5 minutes.

12. A method of applying a liner around an implant cylinder anchored into a jaw bone including the steps of (i) blending the components of an elastomeric material to form a resultant mixture, and (ii) applying the resultant mixture around the surface of the implant for forming a liner around the implant.

13. The method of claim 12 wherein the elastomeric material is a methyl methacrylate free material.

14. The method of claim 12 including applying a sealer over the liner to create a non-absorbent surface seal and glaze.

15. The method of claim 12 wherein the components comprise a powder component and a liquid component which are mixed until all of the powder particles are totally moistened.

16. The method of claim 15 wherein the powder component is polyethylmethacrylate, the liquid component being Di-n-butyl phthalate, ethyl acetate and ethyl alcohol, and the sealer being a polyvinyl chloride/polyvinyl acetate copolymer dissolved in a methyl ethyl ketone solvent.

17. The method of claim 12 wherein the liner forms a gasket around the implant.

18. The method of claim 12 wherein the method is carried out at dental chairside.

19. The method of claim 18 wherein the resultant mixture cures in the mouth in about 5 minutes.

20. A method of applying a liner around a healing cap anchored into a jaw bone including the steps of (i) blending the components of an elastomeric material to form a resultant mixture, and (ii) applying the resultant mixture around the surface of the cap for forming a liner around the cap.

21. The method of claim 20 wherein the liner forms a gasket around the healing cap.

* * * * *